(12) United States Patent
Faries, Jr.

(10) Patent No.: US 8,734,405 B2
(45) Date of Patent: *May 27, 2014

(54) LAY FLAT TUBING

(75) Inventor: Durward I. Faries, Jr., Las Vegas, NV (US)

(73) Assignee: Patented Medical Solutions, LLC, Las Vegas, NV (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/359,859

(22) Filed: Jan. 27, 2012

(65) Prior Publication Data

US 2012/0191050 A1 Jul. 26, 2012

Related U.S. Application Data

(63) Continuation of application No. 11/081,718, filed on Mar. 17, 2005.

(51) Int. Cl.
*A61M 5/00* (2006.01)
(52) U.S. Cl.
USPC .......................... 604/257; 604/921; 128/912
(58) Field of Classification Search
USPC ....... 604/257, 523, 921; 220/DIG. 7; 128/912
See application file for complete search history.

(56) References Cited

U.S. PATENT DOCUMENTS

| | | |
|---|---|---|
| 2,990,875 A | 7/1961 | Samuels et al. |
| 3,927,671 A | 12/1975 | Chittenden et al. |
| 4,532,414 A | 7/1985 | Shah et al. |
| 5,013,308 A | 5/1991 | Tamari et al. |
| 5,103,817 A | 4/1992 | Reisdorf et al. |
| 6,641,602 B2 | 11/2003 | Balding |
| 6,824,528 B1 | 11/2004 | Faries, Jr. et al. |
| 7,608,460 B2 | 10/2009 | Reed et al. |
| 7,942,851 B2 | 5/2011 | Faries, Jr. et al. |
| 8,226,293 B2 | 7/2012 | Faries, Jr. et al. |
| 8,226,605 B2 | 7/2012 | Faries, Jr. et al. |
| 8,313,462 B2 | 11/2012 | Faries, Jr. et al. |
| 8,444,599 B2 | 5/2013 | Faries, Jr. et al. |
| 2005/0070845 A1 | 3/2005 | Faries, Jr. et al. |
| 2008/0147016 A1 | 6/2008 | Faries, Jr. et al. |
| 2010/0168671 A1 | 7/2010 | Faries, Jr. et al. |
| 2012/0053518 A1 | 3/2012 | Faries, Jr. et al. |
| 2012/0191050 A1 | 7/2012 | Faries, Jr. |
| 2013/0197437 A1 | 8/2013 | Faries et al. |

FOREIGN PATENT DOCUMENTS

| | | |
|---|---|---|
| CA | 2103791 | 10/1993 |
| GB | 2274514 A | 7/1994 |

*Primary Examiner* — Theodore Stigell
*Assistant Examiner* — Deanna K Hall
(74) *Attorney, Agent, or Firm* — Edell, Shapiro & Finnan, LLC

(57) ABSTRACT

Lay flat tubing is used as a fluid conductor for transferring fluid to and from the body of a patient. The lay flat tubing lies flat or collapsed when not in use, utilizing minimal space during transportation and storage, but which expands to form a passage when used to conduct fluid. A plurality of lumens may be formed in the lay flat tubing. At least one lumen transports infused fluid end-to-end from a source to an entry site on a patient, or in the alternative from an entry site on or in a patient. All lumens are isolated with respect to each other in order to prevent crossover of fluid from one lumen to the other.

4 Claims, 6 Drawing Sheets

LAY FLAT TUBING

CROSS-REFERENCE TO RELATED APPLICATIONS

This application is a Continuation of U.S. patent application Ser. No. 11/081,718, entitled "Lay Flat Tubing" and filed Mar. 17, 2005, the disclosure of which is incorporated herein by reference in its entirety.

BACKGROUND OF THE INVENTION

1. Technical Field

The present invention pertains to methods and apparatus for conducting fluid to and from the body of a living being. In a particular embodiment, the present invention is directed toward methods and apparatus for infusing of one or more liquids into a patient and/or conducting such fluid(s) from a patient. The present invention is further directed to methods and apparatus for transferring information via a conductive material in a common structure with fluid-conductive tubing.

2. Discussion of Prior Art

Generally, intravenous ("I.V.") solutions or other liquids are infused into a patient by disposing a liquid-filled bag containing the intravenous solution or other liquid on a support structure, e.g., a pole, that permits either gravitational forces or the application of additional pressure to direct liquid from the bag through a preformed cylindrical tube into a patient.

Invariably, patients require infusion of one of more I.V. solutions during the course of their treatment. Accordingly, first responders and hospitals require that large amounts of tubing be stored in anticipation of treatment, thereby creating an issue of storage space adequacy. Hospitals and, more critically, ambulances have limited storage space for necessary medical supplies.

Similarly, storing I.V. tubing with its ends open and exposed to the ambient environment creates a contamination risk by unintentionally allowing micro-organisms, pyrogens, particulates, and other contaminants to enter and contact an inner surface of the intravenous tubing.

Furthermore, treatment may require that several tubes be connected to a patient at a single time. In addition to intravenous tubes, it may be necessary to connect other standalone lines to or near a patient, e.g., wire leads for warming the I.V. solution, conductive wiring for monitoring the patient's body functions, etc. The application of multiple standalone lines coupled with intravenous tubes to treat a patient can be confusing to a caregiver and may result in incorrect deployment and treatment. Moreover, manipulation of multiple lines can create a tangle and cause additional damage. Several organizational apparatuses attempt to manage multiple lines and tubes leading to a patient. These devices characteristically include a locking bar with several tube-receiving recesses that allow a caregiver to separate and label the independent lines and tubes. Such devices suffer from several drawbacks. As a first responder, a caregiver may not have the time to properly setup and/or label each line administered. Also, the devices are yet an additional item to manage and store during treatment.

As previously stated, infusion of intravenous fluids often relies on gravitational forces to infuse the contents of a liquid-filled bag into a patient. However, gravitational forces may be insufficient to drive certain viscous liquids, such as blood, into the patient at the necessary flow rate. There are several examples of prior art attempts to alleviate the aforementioned problem. For example, U.S. Pat. No. 4,090,514 (Hinck et al.) discloses a pressure infusion device including a bladder wherein the device encases a liquid-filled bag with the bladder surrounding at least eighty percent of that bag. Upon inflation of the bladder, liquid within the liquid-filled bag is infused under pressure into a patient. Further, U.S. Pat. No. 4,551,136 (Mandl) discloses a pressure infuser including an inflatable bladder that wraps about a bag. The bladder includes a vertical strip at each end and a strap that wraps about the bladder and bag. The vertical strips overlap to provide a complete wrap about the liquid-filled bag, while the strap maintains contact between the overlapping strip portions. The bladder is inflated to a desired pressure whereby pressure is applied by the bladder to the liquid-filled bad to infuse liquid into a patient.

Moreover, it is desirable during surgical procedures to maintain a patient's normal body temperature to avoid hypothermia and other complications brought about by the infusing liquids having temperatures below normal body temperature. Such complications include, but are not limited to, a decrease in patient body temperature, shock, cardiac dysfunction, increased coagulation time, and, in certain patients, an agglomeration of blood cells.

In order to avoid hypothermia and other complications as described above, warmers are typically employed during surgical and other medical procedures to maintain the infused liquid temperature at or near body temperature. Some examples include: U.S. Pat. No. 1,995,302 ("Goldstein"), utilizing a spirally wound electric resistance wire about the outer surface of an I.V. line; U.S. Pat. No. 3,247,851 ("Seibert"), disclosing a heating sleeve surrounding and extending along a length of tube to heat liquid as the liquid flows to a receptacle; and, U.S. Pat. No. 5,250,032 ("Carter, Jr. et al.") teaching a housing having a channel for receiving a portion of an intravenous tube and a heating element mounted proximate a slot disposed within the channel to heat the tube.

The prior art warmer systems briefly described above suffer from several disadvantages. In particular, those systems tend to employ and control a single independent heating element disposed along a tube. This limits control accuracy of the liquid temperature, creating hotspots, i.e., sections of the tube being warmer than other sections of the tube, along the tube. Moreover, certain prior art warmer systems heat liquid flowing within an intravenous or other tube at a site located a substantial distance from the infusion location, thereby permitting heated liquid to cool by the time the heated liquid reaches the patient.

OBJECTS AND SUMMARY OF THE INVENTION

Accordingly, it is an object of the present invention to provide lay flat tubing as a fluid conductor for transferring fluid to and from the body of a patient. The lay flat tubing facilitates fluid delivery to or removal from a patient's body at an access point, or can similarly effect the same function from a cavity or organ of a patient.

It is an object of the present invention to provide tubing capable of lying flat or collapsed, utilizing minimal space during transportation and storage, but which expands to form a passage when used to conduct fluid. It is similarly an object to reduce the risk of inner tube surface contamination during transportation and storage.

It is another object of the present invention to minimize the number of independent lines and tubes connected to a patient during a procedure or treatment by utilizing lay flat tubing with two or more lumens running the length thereof, thereby permitting the infusion of multiple mutually exclusive liquids through a single structure.

Yet another object of the present invention is to provide lay flat intravenous tubing with at least one additional lumen capable of enclosing a conductive material capable of carrying an electrical current along the length of the lay flat tubing.

The aforesaid objects are achieved individually and in combination, and it is not intended that the present invention be construed as requiring two or more of the objects to be combined unless expressly required by the claims attached hereto.

According to the present invention, a method and apparatus for infusing liquids utilize lay flat tubing constructed from two sheets of thermoformed polymer bonded together. Alternatively, a single sheet of thermoformed polymer may be longitudinally folded onto itself and subsequently sealed to form the desired lumen. A plurality of lumens may be formed in the same structure by joining the two sheets or the folded single sheet to define suitable seams. The plural lumen structure may also be constructed by bonding a series of longitudinally extending narrow plastic strips onto a wider polymer sheet. The lumens are totally closed and mutually sealed along their lengths and open at their ends.

When not transporting fluids, the tubing lies substantially flat, eliminating any open interior volume and occupying no more space than required by the sheets superimposed on each other un-abutting relation. The sheets are bonded along lineal seams to form the lumens or channels, at least one of which transports infused fluid end-to-end from a source to an entry site on a patient, or in the alternative from an entry site on or in a patient. The fluid is typically in a liquid state, but may also be gaseous or a combination liquid and gas.

While the preferred embodiment is used to conduct (i.e., remove/deliver) flow of medical solutions, the present invention is not limited to medical applications. Any additional channel can similarly transport fluids, or can alternatively encase a conductive material, e.g., wiring, capable of transmitting signals and information. On the other hand, the wiring may be capable of conducting or generating heat, thereby warming the infused fluid within the other channel. All the channels, or lumens, are isolated with respect to each other in order to prevent crossover of fluid from one lumen to the other.

While laying flat in storage, the collapsed tubing minimizes interior contamination from micro-organisms, pyrogens and particulates. To further decrease the risk of contamination, the ends of the tubing are HF/RF sealed upon completion of the manufacturing process.

In use, the lay flat tubing is inflated or distended by either pressurizing the flattened lumen or lumens with the conducted fluid, manipulating the lay flat tubing manually, passing a mandrel through the lumens, or by any other suitable means.

The above and still further objects, features and advantages of the present invention will become apparent upon consideration of the following detailed description of specific embodiments thereof, particularly when taken in conjunction with the accompanying drawings where like reference numerals in the various figures are utilized to designate like components.

BRIEF DESCRIPTION OF THE DRAWINGS

Like reference numerals have been used to identify like elements throughout this disclosure.

DETAILED DESCRIPTION OF THE PREFERRED

Figure 1A:
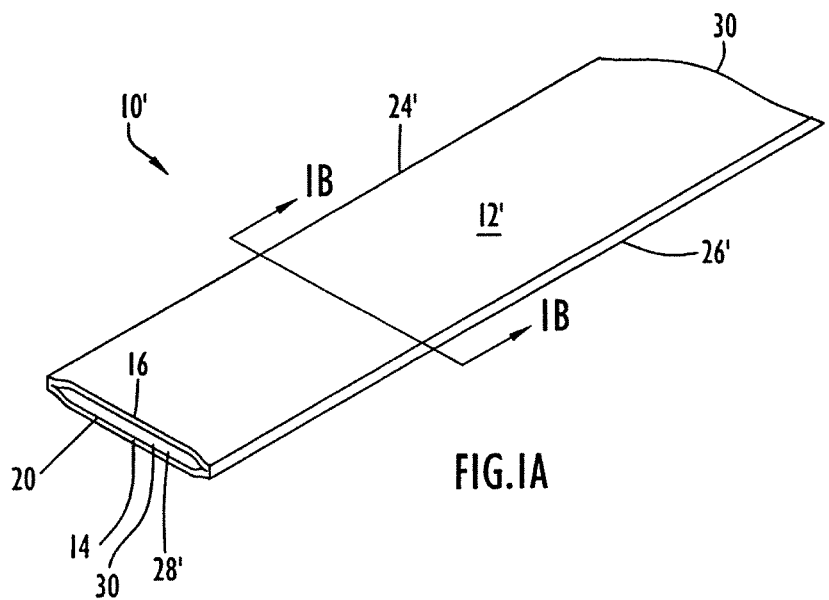
FIG. 1A is a perspective view of a section of a lay flat tubing conduit in accordance with the invention.
Figure 1B:
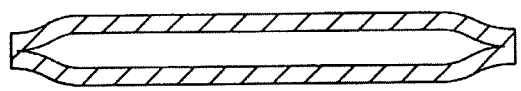
FIG. 1B is a cross-sectional view of the lay flat tubing of FIG. 1A taken along line A-A of FIG. 1A showing the tubing in a collapsed state.
Figure 1C:
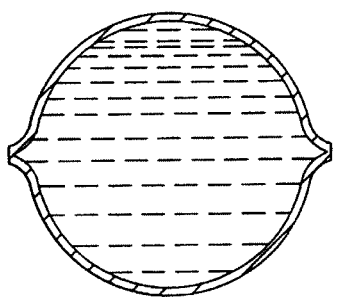
FIG. 1C is a cross-sectional view similar to that in FIG. 1A but showing the tubing in an inflated state.

Referring to FIGS. 1A, 1B and 1C, a conduit unit representing one embodiment of the present invention is constructed of lay flat tubing comprising substantially flat tubing with a single lumen, or conduit, longitudinally disposed the length of the unit. FIGS. 1A and 1B illustrate the lay flat tubing 10 in its collapsed condition as is typical of the tubing during transport and/or storage. FIG. 1C illustrates the unit 10 inflated as by the passage of fluid therethrough. Lay flat tubing 10 has a top conduit layer 12 superimposed on a bottom conduit layer 14. Both layers 12, 14 have are generally shaped as elongated rectangles and are typically compressed together (i.e., the tubing is collapsed) when unit 10 is being stored or transported. It is to be noted that, for ease in understanding the drawings, there is a small space illustrated between layers 12 and 14; however, it will be recognized that in the collapsed state of the conduit the two layers are preferably in abutting, fluid-sealing contact along their lengths.

Both the top conduit layer 12 and the bottom conduit layer 14 have an interior surface and an exterior surface. The top conduit layer 12 and the bottom conduit layer 14 are sealed together along outer parallel longitudinally extended edges 24, 26 forming a lumen 28 between first and second interior surfaces 16, 20 of the top conduit layer 12 and the bottom conduit layer 14, respectively.

The lay flat tubing unit 10 is preferably constructed from a sheet of thermoformed polymer having flexible and at least partially resilient properties. Thermoformed polymer is generally formed as a flat sheet capable of deformation when an additional force or pressure is applied to a surface of the sheet. Once the applied force or pressure is removed, the thermoformed polymer sheet returns to its original shape as a flat sheet.

As seen in FIGS. 1A and 1B, since the interior surfaces 16 and 18 are normally disposed flush against one another in a fluid-sealing relationship, the flow cross-sectional area of lumen 28 is negligible through out the lumen length. Lumen 28 has a pair of longitudinally spaced openings 30 at its ends. While FIGS. 1A and 1B depict the end openings 30 as residing in planes perpendicular to edges 24, 26 of the top and bottom conduit layers 12, 14, the end openings 30 can be provided with an angular relationship to edges 24, 26. End openings 30 of the lumen 28 are also normally fluid-sealed.

As best seen in FIG. 1C, lumen 28 of lay flat tubing 10 expands diametrically in response to the application of an internal pressure or force at either end openings 30. For example, FIG. 1C illustrates fluid 50 providing sufficient pressure to force the interior surfaces of lumen 28 away from one another, thus creating a generally circular cross-sectional profile for the flow passage through the lumen.

Figure 2A:
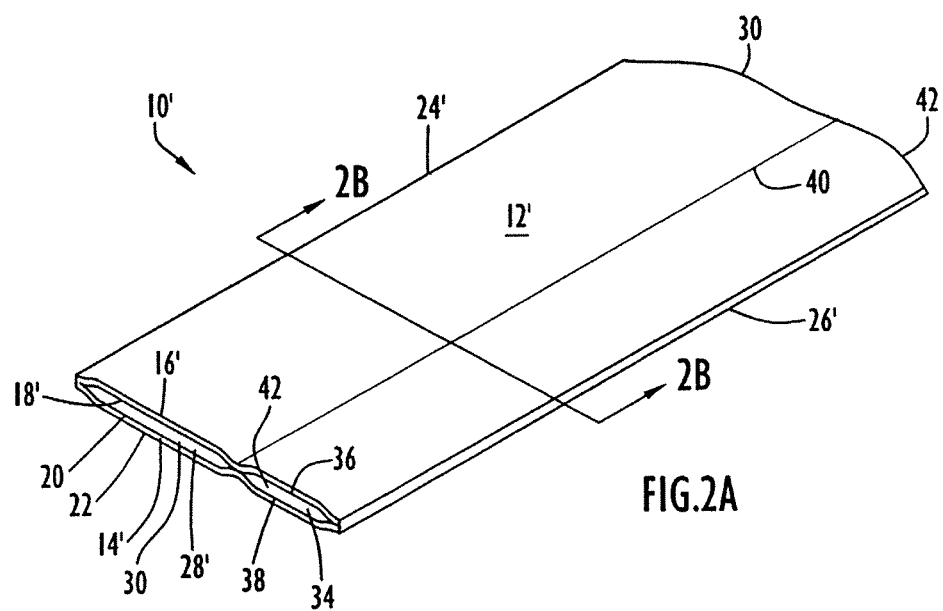
FIG. 2A is a perspective view of a section of a lay flat tubing conduit having two side-by-side lumens shown in a collapsed state in accordance with the invention
Figure 2C:
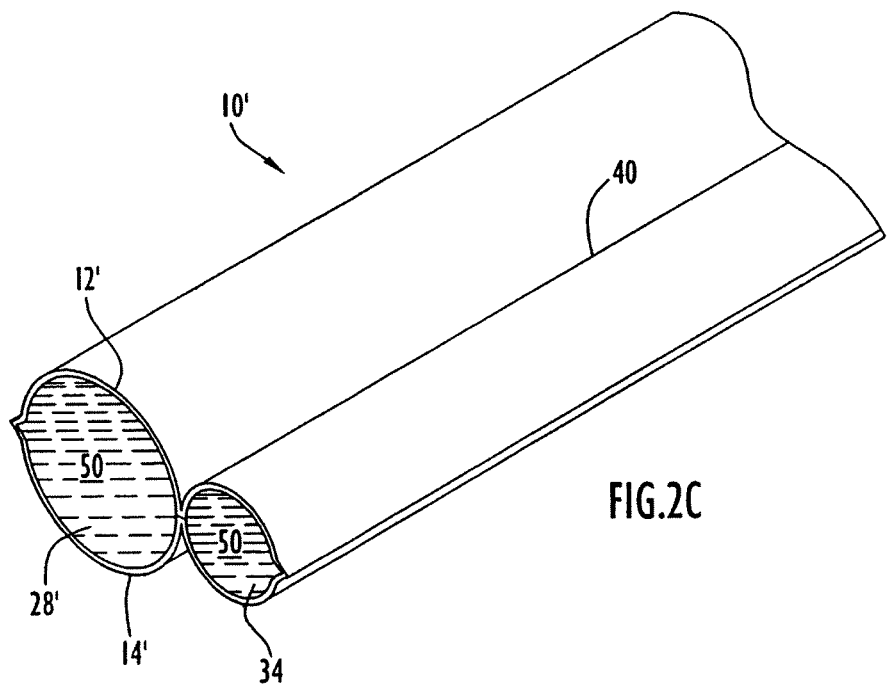
FIG. 2C is a perspective view similar to FIG. 2A but showing the tubing in an inflated state.
Figure 2B:
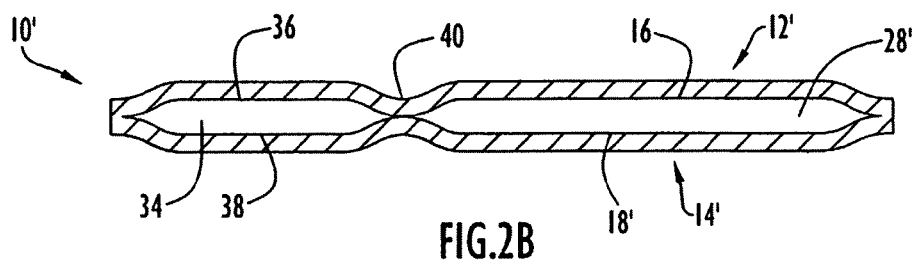
FIG. 2B is a cross-sectional view of the lay flat tubing of FIG. 1A taken along line B-B of FIG. 2A.

Referring to FIGS. 2A-C, an alternative embodiment of the present invention includes lay flat tubing 10' having a top conduit layer 12' superimposed on a bottom conduit layer 14'. Both the top conduit layer 12' and the bottom conduit layer 14' have at least one interior surface and at least one exterior surface. The top conduit layer 12' and the bottom conduit layer 14' are sealed along outer parallel longitudinally extended edges 24', 26' forming a lumen 28' between first and second interior surfaces 16', 20' of the top conduit layer 12' and the bottom conduit layer 14', respectively.

A second lumen 34 is formed by sealing the top conduit layer 12' to the bottom conduit layer 14' along a seam line 40 located parallel to and between the outer longitudinally extended edges 24', 26'. Second lumen 34 is formed from third interior surface 36 of the top conduit layer 12' and fourth interior surface 38 of the bottom conduit layer 14'.

As seen in FIGS. 2A and 2B, the respective first and third interior surfaces 16', 36 of the top conduit layer 12' and the second and fourth interior surfaces 18', 38 of the bottom conduit layer 14' of the lay flat tubing 10' are normally disposed flush against one another in a fluid-sealing relationship; thus the cross-sectional flow area of both first lumen 28' and second lumen 34 throughout the lay flat tubing 10' is negligible as with the embodiment previously described. First lumen 28' has a pair of longitudinally spaced end openings 30' while second lumen 34 has a pair of longitudinal spaced end openings 42. End openings 30', 42 of both first and second lumens 28', 34 are normally disposed to be fluid-sealed along their lengths. As best seen in FIG. 2C, first lumen 28' and second lumen 34 open in response to the application of a pressure or force to any of the spaced openings 30', 42.

First lumen 28' and second lumen 34 are formed as independent conduits, separated by the sealing of seam line 40, in order to prevent inter-mixing of fluid between the lumens. Again, both lumens 28', 34 are sealed longitudinally between end openings 30', 42 for conducting fluid 50. The spatial relationship of lumens 28' and 34 is a function of seam line 40 placement. Thus, creating a larger lumen 28' produces a smaller lumen 34. It is also possible, for some applications to space the lumens 28' and 34 from one another by a section of the lay flat tubing sealed at its ends.

Figure 3:
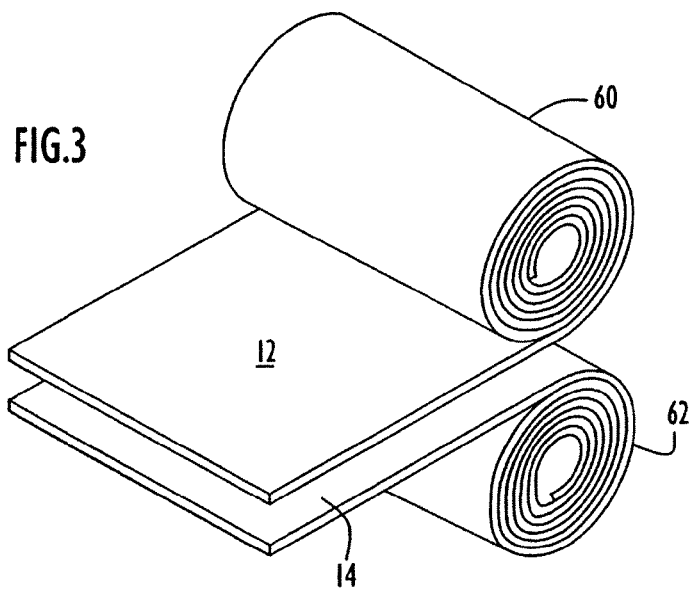
FIG. 3 is a perspective view illustrating a step in the method of manufacturing lay flat tubing according to the present invention.

FIG. 3 illustrates a method of forming the lay flat tubing 10 described hereinabove and illustrated in FIGS. 2A-C. Two rolls 60, 62 of thermoformed polymer sheet material are placed so that as the top conduit layer 12' and the bottom conduit layer 14' are withdrawn, they are positioned one on top of the other in flush abutting relation for subsequent sealing during lumen formation. Alternatively, the substantially equal lengths of thermoformed polymers can be positioned one on top of each other. The two layers 12', 14' are then sealed in accordance with the above-described arrangement (i.e., sealing along parallel longitudinally extended edges 24', 26' and a seam line 40).

The method of sealing or bonding the layers together can be selected from heat sealing, ultrasonic welding, dielectric welding, extrusion during sheet formation or other methods known to persons skilled in the art. The lumens 28, 28', 34 of the lay flat tubing 10 should be capable of withstanding a minimum internal pressure in the range of about one hundred pounds per square inch (100 psi).

Figure 4:
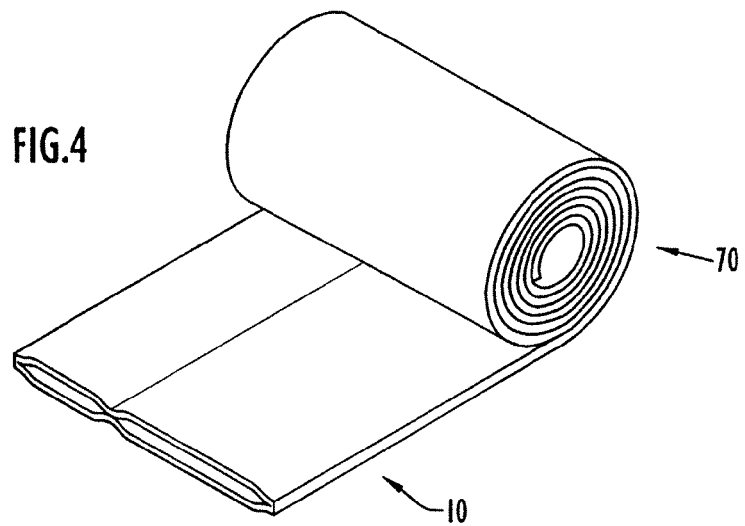
FIG. 4 is a perspective view of a roll of collapsed lay flat tubing according to the present invention.

The nature of the lay flat tubing 10 after manufacturing permits the tubing 10 to be stored and transported in a roll 70 configuration as seen in FIG. 4, either with or without a winding mandrel. Thus, a roll 70 of lay flat tubing 10 occupies a minimal amount of space as compared to pre-formed tubing that includes open flow regions. As lay flat tubing 10 is required for use, the necessary length can be extracted from the roll 70 and cut accordingly. Alternatively, pre-cut sections may be supplied and stored in stacks, again minimizing the storage space required since the flow areas are closed.

Figure 5A:
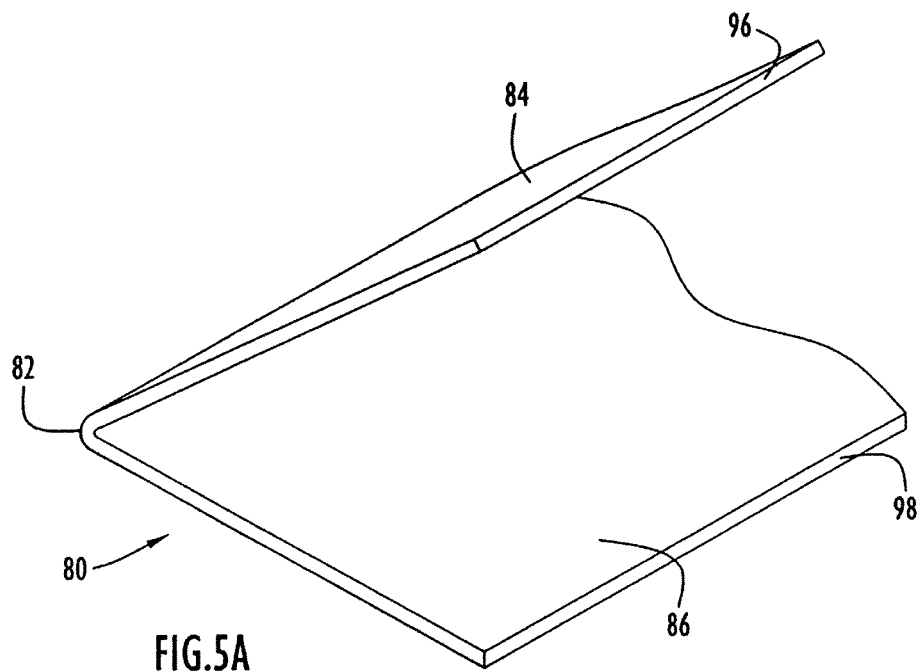
FIG. 5A is a perspective view of a step in the manufacture of an alternate embodiment of the lay flat tubing of the present invention.
Figure 5B:
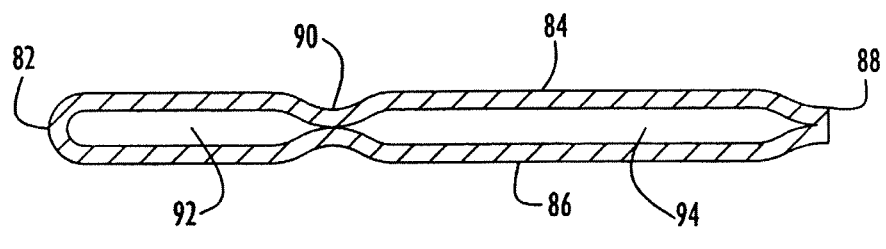
FIG. 5B is a cross-sectional view of the alternate embodiment of FIG. 5A showing two lumens in their collapsed state.

An alternative method of manufacturing the lay flat tubing is illustrated in FIGS. 5A and 5B. A single sheet 80 of a thermoformed polymer is drawn or extruded. Sheet 80 is folded in half creating a longitudinal fold line 82 situated between a top half 84 and a bottom half 86 of the sheet 80. The longitudinally extended edges 96, 98 of the top and bottom halves 84, 86 are aligned and sealed together so that the resultant edge seam 88 is parallel to fold line 82. Similarly, bonding along a longitudinal line creates a seam line 90 parallel to both the edge seam 88 and the fold line 82 to create two lumens 92, 94.

Figure 6A:
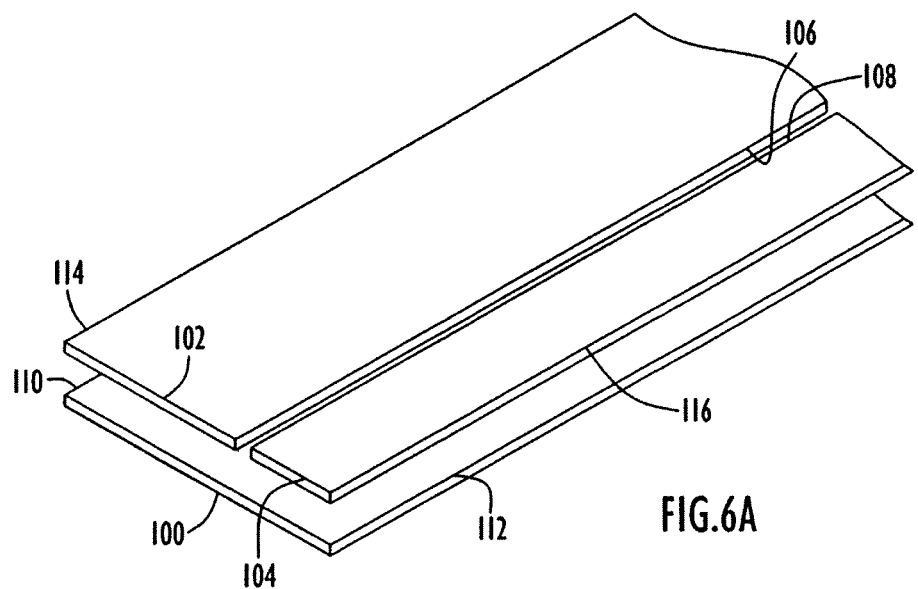
FIG. 6A is a perspective view of a step in the manufacture of another alternate embodiment of the lay flat tubing of the present invention.
Figure 6B:
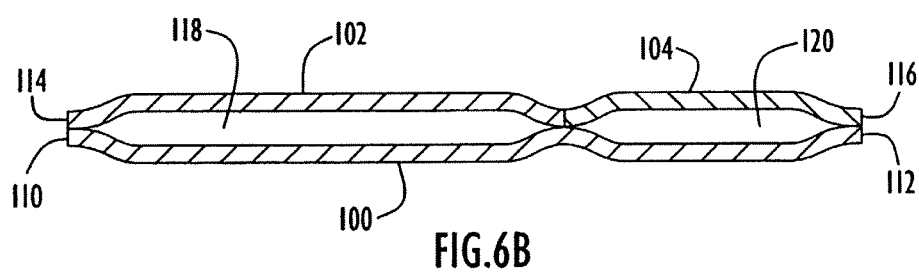
FIG. 6B is a cross-sectional view of the embodiment of FIG. 6A showing two lumens in their collapsed state.

FIGS. 6A and 6B illustrate yet an additional embodiment for manufacturing the lay flat tubing 10 described in relation to FIGS. 2A-C. FIG. 6A illustrates an elongated rectangular base layer 100 onto which is superimposed a pair of separate sheets 102, 104. Here again, the base layer 100 and the pair of sheets 102, 104 are made of thermoformed polymers. Sheets 102, 104 are oriented side by side, such that adjacent longitudinal edges 106, 108 are in contact or nearly contacting one another, and positioned onto the base layer 100. The longitudinal edges 110, 112 of the base layer 100 align with outboard longitudinal edges 114, 116 of the pair of sheets 102, 104, respectively. The respective edges are then sealed to one another in order to form two parallel lumens 118, 120 that run longitudinally along the entire length of the lay flat tubing.

Figure 7:
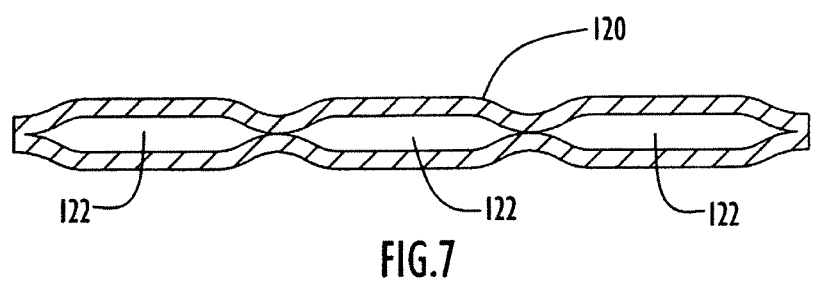
FIG. 7 is a cross-sectional view of still another alternate embodiment of the lay flat tubing of the present invention having three parallel longitudinal lumens shown in their collapsed state.

While the embodiments described above illustrate a lay flat tubing with a two lumens running longitudinally the length of the lay flat tubing, one skilled in the art will recognize that the lay flat tubing can be constructed with more than two lumens, as seen in FIG. 7. Here, the lay flat tubing 120 has a series of three parallel lumens 122 running longitudinally the length of the lay flat tubing 120. Lumens 122 can be formed in any of the above described methods or combination thereof. Similarly, any plurality of lumens can be created in the lay flat tubing.

Furthermore, the lay flat tubing can be treated during and after manufacturing with HF/RF treatment to decrease risk of contamination from micro-organisms, pryogens and particulates. The flush or abutting relationship of the lay flat tubing prevents any of the aforementioned contaminants from residing in the lumens.

Figures 8, 9:
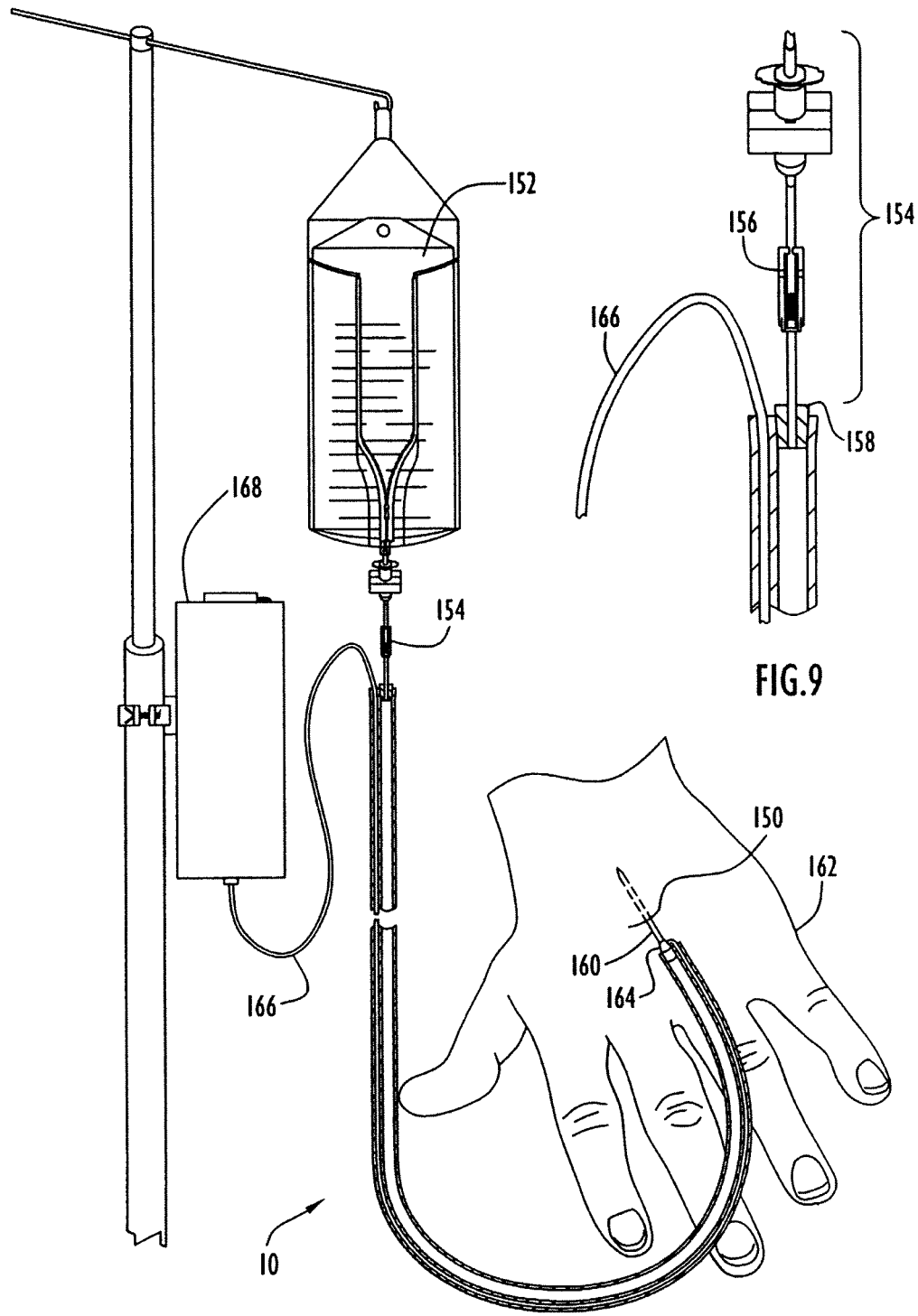
FIG. 8 is a view in perspective of the lay flat tubing of the present invention used in an intravenous delivery system.
FIG. 9 is partial view in perspective of the system of FIG. 8.

FIG. 8 illustrates a method of application for the lay flat tubing 10 as described in FIGS. 1-7. An infusion site 150 on a patient 162 requiring infusion of intravenous fluid is created with a catheter 160. A bag 152 containing a solution of intravenous fluid is located in the vicinity of the patient 162, normally no more than a few feet. The bag 152 has a drip control mechanism 154 attached that controls the flow of intravenous fluid from the bag 152.

FIG. 9 illustrates the drip mechanism 154 and the connection to the lay flat tubing 10. The drip mechanism 154 includes a stopcock 156 for controlling the flow from the bag 150 through drip mechanism 154 into the lay flat tubing 10. A frustoconical member 158 is located at the output end on the drip mechanism 154. The frustoconical member 158 engages a desired spaced opening, for example spaced opening 30, of the lay flat tubing 10. The frustoconical member 158 provides an application of force to the spaced opening 30, causing the spaced opening 30 of the lay flat tubing 10 to deform from a fluid-sealed disposition to a position following the circumferential contours of the frustoconical member 158. The resilient quality of the thermoformed polymer material from which the lay flat tubing 10 is constructed allows the spaced opening 30 to distend. The elastic deformation of distended spaced opening 30 creates a frictional engagement with the frustoconical member 158 and prevents the lay flat tubing 10 from uncoupling with the frustoconical member 158.

Referring once again to FIG. 8, the catheter 160 is inserted at the infusion site 150 on a patient 162. Normally, the catheter 160 is inserted into a vessel or cavity and then fluid is transported into or from a person's body. While one end of the catheter 160 is designed to interact with a patient 162 at the infusion site 150, the other end of the catheter 160 has an attachment point 164 designed to receive a conduit, such as the lay flat tubing 10, through which fluid is conducted. The attachment point 164 is inversely tapered in a manner similar to frustoconical member 158. The spaced opening 30, opposite of the spaced opening attached to the frustoconical member 158, is then frictionally engaged with the attachment point 164. As fluid flows from the bag 152, through the drip mechanism 154 into the lay flat tubing 10, the fluid forces the expansion of the lumen 28 within the lay flat tubing 10 from their fluid sealing relationship.

Further, the embodiment illustrated in FIG. 8 includes one or more electrical signal wires 166 housed within the entire length of the second lumen 34. The wires 166 are made from a material that is preferably electrically conductive and are used to convey electrical current between its ends. At one end the wires 166 can be attached to a monitoring device 168 while at the other end they are attached proximate the infusion site 150, whether to the catheter 160 or the patient 162. Information, such as body temperature, can be transmitted via the wires 166 in the form of electrical signals. Yet another embodiment of the wiring arrangement utilizes the wires 166 to conduct heat along the length of the lay flat tubing. The transferred heat can be used to warm an intravenous solution from the bag 152 as it travels the length of the lumen 28. The wires 166 are either inserted into at least one of the lumens of the lay flat tubing 10 after manufacturing, or the lay flat tubing 10 is formed with the wire 166 disposed between two layers of thermoformed polymers prior to sealing the layers to one another. Yet another embodiment includes a fiber optic cable for transmitting optical signals through the lumen.

While FIG. 8 illustrates use of the lay flat tubing in combination with an intravenous setup, the scope of applications of the lay flat tubing is more expansive. The lay flat tubing can also be used in a surgical procedure wherein the tubing is inserted into a cavity (e.g., lungs, organ, etc.) to extract (e.g., surgical wound drainage) or introduce fluid (e.g., liquid, air, etc) via one or more lumens. Similarly, the lay flat tubing can be used in veterinary procedures as well.

As noted above, in addition to supplying the lay flat tubing in rolls, the tubing may be pre-cut to specified lengths. In addition, the individual lengths of tubing may be provided with suitable connectors or other specified termination. For example, conventional fluid connectors, such as Luer-Locks, may be attached as terminations at the ends of the pre-cut sections of lay flat tubing. Likewise, conventional electrical connectors may be attached at the tubing ends for lumens that carry electrical wiring.

As noted above, it is contemplated that lumens formed as part of the same lay flat tubing structure may be separated from one another by transversely spaced seams, thereby forming a web that spaces the lumens transversely from one another by any desired distance. The web portion(s) residing between the lumens may be cut at the time of manufacture or at the time of installation of the tubing to facilitate relative movement between the ends of the lumens to thereby enable their connection to different locations. Rather than cutting the web it may be perforated to facilitate separation of the lumens at their ends.

It is also contemplated that the lay flat tubing of the present invention may be provided as part of a fluid sensing package (e.g., fluid flow sensor, fluid temperature sensor, etc.) wherein the tubing is permanently connected to the sensor with sensor probes, wiring, etc., inserted into lay flat tubing at the ends of the lumens or anywhere along the lumen lengths.

Having described preferred embodiments of lay flat tubing assemblies and methods of manufacture, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

The invention claimed is:

1. A conduit, comprising:
   a tubular member including first and second conduit walls having parallel longitudinally extending, transversely spaced edges joined together in fluid-sealing relation; and
   a seam line defined in said tubular member to form first and second lumens within said tubular member that are attached to each other along a side edge of said lumens, each lumen having interior and exterior surfaces and longitudinally spaced first and second open terminal ends but is otherwise fluid sealed along its length, and said seam line extending within said tubular member between said attached first and second lumens from said first open terminal end of said attached lumens to said second open terminal end of said attached lumens;
   wherein said interior surfaces, in the absence of applied pressure therebetween, are normally disposed substantially flush against one another, each of said first and second lumens being responsive to pressure applied between interior surfaces such that said interior surfaces expand away from one another;
   wherein said first lumen is configured to conduct fluid from a fluid source to a desired location and said first open terminal end of said first lumen serves as an inlet and is configured to attach to said fluid source to receive fluid therefrom and said second open terminal end of said first lumen serves as an outlet and is configured to deliver said fluid to said desired location; and wherein said conduit further comprises at least one electrical conductor extending longitudinally through said second lumen.

2. A conduit, comprising:

a tubular member including first and second conduit walls having parallel longitudinally extending, transversely spaced edges joined together in fluid-sealing relation;

a seam line defined in said tubular member to form first and second lumens within said tubular member that are attached to each other along a side edge of said lumens, each lumen having interior and exterior surfaces and longitudinally spaced first and second open terminal ends but is otherwise fluid sealed along its length, and said seam line extending within said tubular member between said attached first and second lumens from said first open terminal end of said attached lumens to said second open terminal end of said attached lumens; and at least one fiber optic cable extending longitudinally through said second lumen to transmit optical signals through said second lumen;

wherein said interior surfaces, in the absence of applied pressure therebetween, are normally disposed substantially flush against one another, each of said first and second lumens being responsive to pressure applied between interior surfaces such that said interior surfaces expand away from one another; and wherein said first lumen is configured to conduct fluid from a fluid source to a desired location and said first open terminal end of said first lumen serves as an inlet and is configured to attach to said fluid source to receive fluid therefrom and said second open terminal end of said first lumen serves as an outlet and is configured to deliver said fluid to said desired location.

3. A method for constructing a conduit, the method comprising the steps of:

providing first and second conduit walls having parallel longitudinally extending, transversely spaced edges;

joining respective said transversely spaced edges of said first and second conduit walls together in fluid-sealing relation to form a tubular member;

defining a seam line in said tubular member to form first and second lumens within said tubular member that are attached to each other along a side edge of said lumens, each lumen having interior and exterior surfaces and longitudinally spaced first and second open terminal ends but is otherwise fluid sealed along its length, and said seam line extending within said tubular member between said attached first and second lumens from said first open terminal end of said attached lumens to said second open terminal end of said attached lumens; and extending at least one electrical conductor longitudinally through said second lumen;

wherein said interior surfaces, in the absence of applied pressure therebetween, are normally disposed substantially flush against one another, each of said first and second lumens being responsive to pressure applied between interior surfaces such that said interior surfaces expand away from one another;

wherein said first lumen is configured to conduct fluid from a fluid source to a desired location and said first open terminal end of said first lumen serves as an inlet and is configured to attach to said fluid source to receive fluid therefrom and said second open terminal end of said first lumen serves as an outlet and is configured to deliver said fluid to said desired location.

4. A method for constructing a conduit, the method comprising the steps of:

providing first and second conduit walls having parallel longitudinally extending, transversely spaced edges;

joining respective said transversely spaced edges of said first and second conduit walls together in fluid-sealing relation to form a tubular member;

defining a seam line in said tubular member to form first and second lumens within said tubular member that are attached to each other along a side edge of said lumens, each lumen having interior and exterior surfaces and longitudinally spaced first and second open terminal ends but is otherwise fluid sealed along its length, and said seam line extending within said tubular member between said attached first and second lumens from said first open terminal end of said attached lumens to said second open terminal end of said attached lumens; and extending at least one fiber optic cable longitudinally through said second lumen to transmit optical signals through said second lumen;

wherein said interior surfaces, in the absence of applied pressure therebetween, are normally disposed substantially flush against one another, each of said first and second lumens being responsive to pressure applied between interior surfaces such that said interior surfaces expand away from one another;

wherein said first lumen is configured to conduct fluid from a fluid source to a desired location and said first open terminal end of said first lumen serves as an inlet and is configured to attach to said fluid source to receive fluid therefrom and said second open terminal end of said first lumen serves as an outlet and is configured to deliver said fluid to said desired location.

* * * * *